US010870857B2

United States Patent
Hahm et al.

(10) Patent No.: US 10,870,857 B2
(45) Date of Patent: Dec. 22, 2020

(54) METHOD OF PRODUCING GINSENOSIDES 20(S)-RG3 AND 20(S)-RH2 USING GINSENOSIDE GLYCOSIDASES

(71) Applicants: MODNBIO, INC., Seoul (KR); Eun Kyung Do, Gyeonggi-do (KR)

(72) Inventors: Jong Cheon Hahm, Daejeon (KR); Eun Kyung Do, Gyeonggi-do (KR)

(73) Assignee: Modnbio, Inc., Seoul (KR)

( * ) Notice: Subject to any disclaimer, the term of this patent is extended or adjusted under 35 U.S.C. 154(b) by 5 days.

(21) Appl. No.: 16/213,729

(22) Filed: Dec. 7, 2018

(65) Prior Publication Data
US 2019/0194667 A1 Jun. 27, 2019

Related U.S. Application Data

(63) Continuation of application No. PCT/KR2017/014307, filed on Dec. 7, 2017.

(30) Foreign Application Priority Data

Oct. 20, 2017 (KR) .................. 10-2017-0136202

(51) Int. Cl.

| | |
|---|---|
| *A61K 38/47* | (2006.01) |
| *C12N 15/52* | (2006.01) |
| *C12N 15/74* | (2006.01) |
| *C12P 33/00* | (2006.01) |
| *C12N 9/42* | (2006.01) |
| *C12N 9/26* | (2006.01) |
| *C12P 33/20* | (2006.01) |

(52) U.S. Cl.
CPC ........... *C12N 15/52* (2013.01); *C12N 9/2408* (2013.01); *C12N 9/2445* (2013.01); *C12N 15/74* (2013.01); *C12P 33/00* (2013.01); *C12P 33/20* (2013.01); *C12Y 302/01* (2013.01); *C12Y 302/01021* (2013.01)

(58) Field of Classification Search
None
See application file for complete search history.

(56) References Cited

FOREIGN PATENT DOCUMENTS

KR    20140006683    1/2015

OTHER PUBLICATIONS

Bae et al. (Biol. Pharm. Bull., vol. 25(1), No. 1, pp. 58-63, 2002).*
Bae et al., Transformation of Ginseng Saponins to Ginsenoside Rh2 by Acids and Human Intestinal Bacteria and Biological Activities of Their Transformants, Arch Pharm Res, 27(1):61-67 (2004).
Behrendt et al., Reclassification of Leifsonia ginsengi (Qiu et al. 2007) as *Herbiconiux ginsengi* gen. nov., comb. nov. and description of *Herbiconiux solani* sp. nov., an actinobacterium associated with the phyllosphere of Solanum tuberosum L., Intl J. Systematic and Evolutionary Microbiology, 61:1039-1047 (2011).
International Search Report and Written Opinion for Int. App No. PCT/KR2017/014307, dated Jul. 24, 2018 (8 pages) [With English Translation].
NCBI Reference Sequence: WP_012025502.1, beta-glucosidase BglX [Flavobacterium johnsoniae] dated May 11, 2018 (2 pages).
NCBI Reference Sequence: WP_092557307.1, glycosyl hydrolase [Herbiconiux ginsengi] dated Nov. 14, 2017 (2 pages).

\* cited by examiner

*Primary Examiner* — Hope A Robinson
(74) *Attorney, Agent, or Firm* — Fish & Richardson P.C.

(57) ABSTRACT

The present invention relates to a method of producing ginsenoside 20(S)—Rg3 or 20(S)—Rh2 using a novel ginsenoside glycosidase in order to obtain ginsenoside 20(S)—Rg3 or 20(S)—Rh2 with high efficiency and high purity. According to the production method of the present invention, a large amount of 20(S)—Rg3 or 20(S)—Rh2, which is a minor form of rare ginsenoside present in very small amounts in ginseng or processed ginseng products, may be safely and efficiently produced. In particular, the method according to the present invention has an advantage in that it may produce a large amount of 20(S)—Rg3 or 20(S)—Rh2 for industrial applications, since the process is very simple and the production efficiency is very high.

13 Claims, 3 Drawing Sheets

Specification includes a Sequence Listing.

METHOD OF PRODUCING GINSENOSIDES 20(S)-RG3 AND 20(S)-RH2 USING GINSENOSIDE GLYCOSIDASES

SEQUENCE LISTING

The instant application contains a Sequence Listing which has been submitted electronically in ASCII format and is hereby incorporated by reference in its entirety. Said ASCII copy, created on Jan. 9, 2019, is named 47639-0002001.txt and is 19,812 bytes in size.

TECHNICAL FIELD

The present invention relates to a method of producing ginsenoside 20(S)—Rg3 or 20(S)—Rh2 using a novel ginsenoside glycosidase derived from *Herbiconiux ginsengi* or *Flavobacterium johnsoniae* in order to obtain ginsenoside 20(S)—Rg3 or 20(S)—Rh2 with high efficiency and high purity.

BACKGROUND ART

Saponins refer to substances in which the non-sugar moiety is composed of polycyclic compound in the glycoside widely distributed in the plant kingdom. Triterpene saponin, contained in ginseng or red ginseng as a major physiologically active ingredient, has a chemical structure different from those of saponins found in other plants, and thus this ginseng saponin is called ginsenoside which means ginseng glycoside, in order to distinguish it from saponins found in other plants.

Ginsenosides may be classified into three groups based on their aglycone structure: Protopanaxadiol (PPD)-type ginsenosides, Protopanaxatriol (PPT)-type ginsenosides, and Oleanolic acid-type ginsenosides. These three groups are further classified based on the position and number of sugar moieties attached by a glycosidic bond at C-3, C-6, and C-20 positions of the rings in the chemical structure. The basic skeleton of the oleanolic acid-type ginsenoside is a pentacyclic backbone, which is the only ginsenoside Ro, and the aglycon is oleanolic acid. To date, more than 180 species of ginsenosides have been isolated, and most of them are PPD-type ginsenosides. The PPD-type ginsenosides include Rb1, Rb2, Rb3, Rc, Rd, Gypenoside XVII, Compound O, Compound Mc1, F2, Compound Y, Compound Mc, Rg3, Rh2, and C—K. The PPT-type ginsenosides include Re, Rg1, Rf, Rg2, Rh1, F1, and the like.

In addition, major ginsenosides account for more than 90% of ginsenosides in dried ginseng, but these compounds have the problem of showing a very low absorption rate in vivo because of large size of each compound. Therefore, in order to increase the efficacy of ginsenosides, research and development has been conducted to convert major ginsenosides to minor ginsenosides, including F2, Rg3, Rk1, Rg5, Rh1, Rh2, Rk2, Rh3, gypenoside (Gyp) XVII, gypenoside LXXV, and compound K, Mc, Mc1, and the like, which are relatively easily absorbed and also have better efficacy. For example, studies on the deglycosylation of glucose, arabinose, rhamnose, xylose and the like, which constitute sugar in major ginsenosides such as Rg1, Re, Rb1, Rb2, Rc, Rd and the like, have been conducted for the above-mentioned conversion. However, generally there are problems in that a considerably large loss occurs in this conversion process and the desired minor ginsenoside obtained has a very low purity.

Ginsenoside Rg3, one of minor ginsenosides present in very small amounts in ginseng, is known to have anticancer activity. The ginsenoside Rg3 inhibits lung metastasis, and inhibition of this metastasis is related not only to the inhibition of tumor-induced angiogenesis, but also to the inhibition of invasion and adhesion of cancer cells. In addition, the ginsenoside Rg3 is known to down-regulate NF-kB and AP-1 transcription factors which are involved in inflammation and the like. In addition to the mechanisms as described above, Rg3 is known to reduce intracellular calcium levels, and it was shown that the Rg3 induced apoptosis in colorectal cancers and inhibited the proliferation of cancer cells in prostate cancer and also inhibited cancer cell proliferation and angiogenesis in ovarian cancer when used alone or in combination with cyclophosphamide.

In addition to the anticancer effects as described above, the ginsenoside Rg3 is known to exhibit anti-obesity effects by inhibiting the AMPK (AMP-activated protein kinase) signaling pathway and PPAR-$\gamma$. For this reason, the Rg3 has received a lot of attention as a pharmaceutical active ingredient against various diseases including cancer, obesity and the like.

In addition, 20(S)—Rh2, one of minor ginsenosides present in ginseng in very small amounts, is known to be effective in the treatment of brain diseases, such as stroke, due to its effect on brain cell protection. Furthermore, various academic papers discloses that the 20(S)—Rh2 has anticancer effects against various carcinomas, and some studies show that the 20(S)—Rh2 can exhibit therapeutic effects of skin diseases such as chronic dermatitis through its anti-inflammatory effect. Namely, among minor ginsenosides, the 20(S)—Rh2 is known to be used in very various applications, and thus the pharmacological action thereof is attracting attention.

However, the 20(S)—Rg3 and the 20(S)—Rh2 as described above correspond to minor ginsenosides and are contained in ginseng in very small amounts, and thus it is very difficult to extract these two components in large amounts, even when a separate isolation process is performed. Accordingly, various researches and developments have been attempted to isolate and purify these two components in order to use these two components, but fail to isolate these components in sufficient amounts. For example, chemical decomposition methods, enzymatic methods, and methods using glycoside synthesis have been proposed, but these methods known to date still have limitations in mass production, because 1) several steps in the production process should be performed, 2) a large amount of a desired component is lost in the production process, 3) catalysts unsuitable for edible purposes are used, or 4) these methods show low yields.

Regarding the enzymatic methods, many studies have been conducted on biotransformation using various enzymes such as $\alpha$-L-arabinopyranosidase, $\alpha$-L-arabinofuranosidase, $\alpha$-L-rhamnosidase and the like. However, these methods are ineffective for mass production and failed to solve the problem that many costs are incurred. In addition, not all of the above-described enzymes, which may be extracted or isolated from many microorganisms, convert major ginsenosides to minor ginsenosides. In particular, when limited to certain substances such as the 20(S)—Rg3 and the 20(S)—Rh2 as specific ginsenosides, the number of enzymes known to be available is only a few.

Under this background, there is a need for research and development of a method for easily obtaining substances such as the 20(S)—Rg3 and the 20(S)—Rh2, which are rare ginsenosides in minor form present in very small amounts in plants such as ginseng and the like, in high yields and large amounts.

DISCLOSURE

Technical Problem

Therefore, it is a main object of the present invention is to provide a method for safely and efficiently producing a minor form of rare ginsenosides, particularly ginsenosides 20(S)—Rg3 and 20(S)—Rh2, which are present in very small amounts in ginseng or processed ginseng products.

Specifically, an object of the present invention is to provide a method of producing ginsenoside 20(S)—Rg3 by treating ginseng crude saponin with a ginsenoside glycosidase isolated from *Herbiconiux ginsengi*, a transformant introduced with a vector comprising a nucleic acid encoding the ginsenoside glycosidase, or a culture of the transformant.

Another object of the present invention is to provide a method of producing ginsenoside 20(S)—Rh2 comprising the steps of: (a) treating ginseng crude saponin with a ginsenoside glycosidase isolated from *Herbiconiux ginsengi*, a transformant introduced with a vector comprising a nucleic acid encoding the ginsenoside glycosidase, or a culture of the transformant to prepare a reaction solution comprising ginsenoside 20(S)—Rg3; and (b) treating the reaction solution prepared in the step (a) with a ginsenoside glycosidase isolated from *Flavobacterium johnsoniae*, a transformant introduced with a vector comprising a nucleic acid encoding the ginsenoside glycosidase, or a culture of the transformant to produce ginsenoside 20(S)—Rh2.

Still another object of the present invention is to provide a method of producing ginsenoside 20(S)—Rh2 by treating 20(S)—Rg3 with a ginsenoside glycosidase isolated from *Flavobacterium johnsoniae*, a transformant introduced with a vector comprising a nucleic acid encoding the ginsenoside glycosidase, or a culture of the transformant.

Still another object of the present invention is to provide a composition for converting crude saponin to 20(S)—Rg3, the composition comprising a ginsenoside glycosidase comprising an amino acid sequence represented by SEQ ID NO: 3, a transformant introduced with a vector comprising a nucleic acid encoding the ginsenoside glycosidase protein, or a culture of the transformant.

Yet another object of the present invention is to provide a composition for converting crude saponin to 20(S)—Rh2, the composition comprising: a ginsenoside glycosidase comprising an amino acid sequence represented by SEQ ID NO: 3, a transformant introduced with a vector comprising a nucleic acid encoding the ginsenoside glycosidase protein, or a culture of the transformant; and a ginsenoside glycosidase comprising an amino acid sequence represented by SEQ ID NO: 4, a transformant introduced with a vector comprising a nucleic acid encoding the ginsenoside glycosidase protein, or a culture of the transformant.

Technical Solution

The present inventors have made efforts to develop a method for easily obtaining a minor form of rare ginsenosides 20(S)—Rg3 and 20(S)—Rh2, which are present in very small amounts in plants such as ginseng and the like, in high yields and large amounts, and as a result, have completed the present invention by treating ginseng crude saponin, which comprises PPD-type ginsenosides (Rb1, Rb2, Rc, Rd, etc.), with a ginsenoside glycosidase isolated from *Herbiconiux ginsengi* to biotransform the ginseng crude saponin into a large amount of ginsenoside 20(S)—Rg3, and treating the ginsenoside 20(S)—Rg3 with a ginsenoside glycosidase isolated from *Flavobacterium johnsoniae* to biotransform the ginsenoside 20(S)—Rg3 into a large amount of 20(S)—Rh2.

The present invention provides a method of producing ginsenoside 20(S)—Rg3 by treating ginseng crude saponin with a ginsenoside glycosidase isolated from *Herbiconiux ginsengi*, a transformant introduced with a vector comprising a nucleic acid encoding the ginsenoside glycosidase, or a culture of the transformant.

The present invention also provides a method of producing ginsenoside 20(S)—Rh2 comprising the steps of: (a) treating ginseng crude saponin with a ginsenoside glycosidase isolated from *Herbiconiux ginsengi*, or a transformant introduced with a vector comprising a nucleic acid encoding the ginsenoside glycosidase, or a culture of the transformant, to prepare a reaction solution comprising ginsenoside 20(S)—Rg3; and (b) treating the reaction solution prepared in the step (a) with a ginsenoside glycosidase isolated from *Flavobacterium johnsoniae*, a transformant introduced with a vector comprising a nucleic acid encoding the ginsenoside glycosidase, or a culture of the transformant.

The present invention also provides a method of producing ginsenoside 20(S)—Rh2 comprising a step of treating 20(S)—Rg3 with a ginsenoside glycosidase isolated from *Flavobacterium johnsoniae*, a transformant introduced with a vector comprising a nucleic acid encoding the ginsenoside glycosidase, or a culture of the transformant.

In the present invention, *Herbiconiux ginsengi* is a microorganism which is a gram-positive, aerobic, non-mobile bacillus, is mesophilic in nature, and phylogenetically belongs to the family Microbacteriaceae of the phylum Actinobacteria. In the present invention, *Herbiconiux ginsengi* is preferably *Herbiconiux ginsengi* KACC 14262$^T$.

In the present invention, *Flavobacterium johnsoniae* is a microorganism which is gram-negative, bacillus, mesophilic, mobile (via gliding), heterotrophic, and has the property of degrading various polymer substances (chitin, starch, proteins, etc.). In the present invention, *Flavobacterium johnsoniae* is preferably *Flavobacterium johnsoniae* KACC 11414$^T$.

In the present invention, the ginsenoside glycosidase refers to an enzyme that hydrolyzes the glycosidic molecular bond of a disaccharide or longer chained polysaccharide. The degree of activity and function of the ginsenoside glycosidase differ depending on the kind of enzyme. Specifically, the ginsenoside glycosidase isolated from *Herbiconiux ginsengi* according to the present invention has the characteristics of beta-glucosidase. In addition, the ginsenoside glycosidase isolated from *Flavobacterium johnsoniae* according to the present invention has the characteristics of beta-glucosidase.

The ginsenoside glycosidase according to the present invention refers to an enzyme having an activity of either biotransforming ginseng crude saponin comprising PPD-type ginsenosides (Rb1, Rb2, Rc, Rd, etc.) into ginsenoside 20(S)—Rg3, or biotransforming 20(S)—Rg3 into 20(S)—Rh2. In the present invention, the ginsenoside glycosidase may be derived from *Herbiconiux ginsengi* or *Flavobacterium johnsoniae*. Preferably, it may be a ginsenoside glycosidase from *Herbiconiux ginsengi* KACC 14262$^T$ or *Flavobacterium johnsoniae* KACC 11414$^T$. More preferably, it may be a ginsenoside glycosidase comprising an amino acid sequence of SEQ ID NO: 3 or SEQ ID NO: 4. The scope of the present invention may include not only the ginsenoside glycosidase comprising the amino acid sequence of SEQ ID NO: 3 or SEQ ID NO: 4, but also proteins which have an amino acid sequence similarity of at least 90%, more preferably at least 95%, most preferably at least 98%, with the above-described sequence, and which have substantially the same activity as the activity of the ginsenoside glycosidase according to the present invention. In addition, protein variants comprising an amino acid sequence obtained by deletion, modification, substitution or addition of one or more amino acids in the amino acid sequence may fall within the scope of the present invention, as long as they have the sequence similarity as described above and have a biological activity which is substantially identical or similar to that of the ginsenoside glycosidase.

The ginsenoside glycosidase represented by SEQ ID NO: 3 has a remarkable effect on the conversion of crude saponin, preferably PPD-type crude saponin, into 20(S)—Rg3. In particular, as it can produce only 20(S)—Rg3 at high concentration without progression of any additional reaction after conversion from crude saponin into 20(S)—Rg3, it exhibits high efficiency. In addition, it can produce only a water-soluble form of 20(S)—Rg3 in large amounts, and thus produce only 20(S)—Rg3 in large amounts without additional separation of (R)-form and (S)-form. The ginsenoside glycosidase represented by SEQ ID NO: 4 has a remarkable effect on the conversion of 20(S)—Rg3 into 20(S)—Rh2. In particular, even when the ginsenoside glycosidase represented by SEQ ID NO: 4 is added to the corresponding culture immediately after the conversion of crude saponin into 20(S)—Rg3 by use of the ginsenoside glycosidase represented by SEQ ID NO: 3, and is then incubated, it shows high conversion ability, indicating that it makes it possible to perform the reaction without an intermediate purification step, thereby greatly reducing reaction steps and reducing the loss caused by purification. In addition, as it makes it possible to minimize additional reactions after the conversion and can produce 20(S)—Rh2 at high concentration, it shows high efficiency. Furthermore, it can produce only a water-soluble form of 20(S)—Rh2 in large amounts, and thus produce only 20(S)—Rh2 in large amounts without additional separation of (R)-form and (S)-form.

In the present invention, the vector is an expression vector capable of expressing a desired protein in a proper host cell, and refers to a nucleic acid construct comprising essential regulatory elements operably linked to express a nucleic acid insert, preferably the ginsenoside glycosidase according to the present invention. The ginsenoside glycosidase according to the present invention preferably has a nucleotide sequence of SEQ ID NO: 1 or SEQ ID NO: 2.

In one example of the present invention, the ginsenoside glycosidase comprising the nucleotide sequence of SEQ ID NO: 1, derived from *Herbiconiux ginsengi* KACC 14262$^T$, was inserted into the plasmid vector pGEX4T-1 (GE Healthcare, USA) having glutathione S-transferase inserted therein, thereby constructing the recombinant expression vector GST-BglHg. In addition, the ginsenoside glycosidase having the nucleotide sequence of SEQ ID NO: 2, derived from *Flavobacterium johnsoniae* KACC 11414$^T$, was inserted into the plasmid vector pGEX4T-1 (GE Healthcare, USA) having glutathione S-transferase inserted therein, thereby constructing the recombinant expression vector GST-BglFj.

In the present invention, transformation means introducing DNA into a host cell so that the DNA is replicable, either as an extra-chromosomal element or by chromosomal integration. Specifically, it means introducing a foreign DNA into a cell, thereby artificially causing genetic changes. The transformation in the present invention may be performed using any transformation method, and may be performed according to a conventional method known in the art. A transformant introduced with a vector comprising a nucleic acid encoding the ginsenoside glycosidase protein of the present invention according to the above-described transformation method has an activity of bio-transforming crude saponin into ginsenoside 20(S)—Rg3 or bio-transforming ginsenoside 20(S)—Rg3 into ginsenoside 20(S)—Rh2. Specifically, a transformant comprising a ginsenoside glycosidase isolated from *Herbiconiux ginsengi* has a remarkable effect on the conversion of crude saponin to ginsenoside 20(S)—Rg3. In addition, a transformant comprising a ginsenoside glycosidase isolated from *Flavobacterium johnsoniae* has a remarkable effect on the conversion of ginsenoside 20(S)—Rg3 to ginsenoside 20(S)—Rh2.

In the present invention, the host is not particularly limited as long as it expresses the nucleic acid of the present invention. Specific examples of the host that may be used in the present invention include bacteria of the genus *Escherichia*, such as *E. coli* bacteria of the genus Bacillus, such as *Bacillus subtilis*; bacteria of the genus *Pseudomonas*, such as *Pseudomonas putida*; yeasts, such as *Saccharomyces cerevisiae* and *Schizosaccharomyces pombe*; animal cells, and insect cells. The host is preferably *E. coli*, and more preferably *E. coli* BL21 (DE3).

In the present invention, a culture may refer to a product obtained after culturing the transformant according to a known microbial culture method. This product may be a ginsenoside glycosidase isolated from a lysate obtained by collecting and lysing a cultured microorganism. A culture of the transformant introduced with the expression vector comprising the nucleic acid encoding the ginsenoside glycosidase has an activity of converting crude saponin to ginsenoside 20(S)—Rg3 or an activity of converting 20(S)—Rg3 to 20(S)—Rh2.

Ginseng crude saponin refers to a saponin in an unpurified state before being separated into components. Generally, it refers to one comprising a high concentration of Rb1, Rb2, Rc, Rd, etc., obtained by extracting a ginseng sample with a solvent such as ethanol, etc., or by adsorption onto a porous resin. In the present invention, among such ginseng crude saponins, any ginseng crude saponin may be used as long as it comprises Rb1, Rb2, Rc or Rd. This crude saponin may be obtained from the leaves and roots of various ginsengs, including *Panax Ginseng* C. A. Meyer, *Panax quinquefolium* L. and *Panax Japonicum* C. A. Meyer, by extraction with ethanol. More preferably, a crude saponin having an increased content of Rb1, Rb2, Rc or Rd is used, which is obtained by removing sugar and protopanaxatriol-type ginsenosides using a porous resin. According to one embodiment of the present invention, a crude saponin may be a mixture of PPD type ginsenosides, including Rb1, Rb2, Rc, Rd and the like, which may be obtained by extraction with an ethanol solvent, followed by increasing the PPD-type ginsenoside content thereof by adsorption onto a porous resin.

In the present invention, ginsenoside 20(S)—Rg3 refers to one having an S-form at C-20, among minor ginsenosides in which two glucoses (Glc-Glc) are bonded to C-3 in the basic carbon skeleton of a PPD-type saponin. It has the properties of being easily absorbed in vivo due to the removal of sugars and dissolving well in water, unlike the R-form.

In the present invention, ginsenoside 20(S)—Rh2 refers to one having an S-form at C-20, among minor ginsenosides in which one glucose (Glc) is bonded to C-3 in the basic carbon skeleton of a PPD-type saponin. It has the properties of being easily absorbed in vivo due to the removal of sugars and dissolving well in water, unlike the R-form.

The method of producing ginsenoside 20(S)—Rg3 comprising treating ginseng crude saponin with a ginsenoside glycosidase isolated from *Herbiconiux ginsengi*, a transformant introduced with a vector comprising a nucleic acid encoding the ginsenoside glycosidase, or a culture of the transformant, according to the present invention, shows excellent 20(S)—Rg3 productivity, preferably under, but not limited to, conditions described below.

The crude saponin may be used by dissolving in 0.1 M of 0.1 to 2% (w/v) phosphate buffer. In addition, a culture of the transformant introduced with the vector comprising the nucleic acid encoding the ginsenoside glycosidase isolated from *Herbiconiux ginsengi* may be used. More preferably, a ginsenoside glycosidase isolated from a lysate obtained by collecting and lysing cultured *Herbiconiux ginsengi* may be collected and used, and 1 U to 100 U of the ginsenoside glycosidase is preferably used. The incubation may be performed at a pH of 6.0 to 8.0, more preferably 6.5 to 7.5, most preferably about 7.0. The incubation temperature is 28 to 40° C., preferably 30 to 37° C. The incubation time is 12 to 72 hours, more preferably 24 to 48 hours.

After the reaction as described above, the purity of 20(S)—Rg3 may be increased by a conventional additional purification process (e.g., precipitation, re-dissolution, column chromatography, etc.). According to one embodiment of the present invention, the purity of 20(S)—Rg3 is increased using recycling preparative HPLC.

The method of producing ginsenoside 20(S)—Rh2 comprising the steps of: (a) treating ginseng crude saponin with a ginsenoside glycosidase isolated from *Herbiconiux ginsengi*, a transformant introduced with a vector comprising a nucleic acid encoding the ginsenoside glycosidase, or a culture of the transformant to prepare a reaction solution comprising ginsenoside 20(S)—Rg3; and (b) treating the reaction solution prepared in the step (a) with a ginsenoside glycosidase isolated from *Flavobacterium johnsoniae*, a transformant introduced with a vector comprising a nucleic acid encoding the ginsenoside glycosidase, or a culture of the transformant, according to the present invention shows excellent 20(S)—Rg3 productivity, preferably under, but not limited to, conditions described below.

The step (a) is performed under the same conditions as those described above with respect to the method of producing 20(S)—Rg3.

The method may further comprise, before the step (b), a step of performing deactivation of the ginsenoside glycosidase isolated from *Herbiconiux ginsengi*, at 70° C. to 90° C., preferably about 80° C., for at least 4 hours, preferably 6 hours to 12 hours to deactivate the enzyme. A ginsenoside glycosidase isolated from a lysate obtained by collecting and lysing cultured *Flavobacterium johnsoniae* may be used, and 1 U to 100 U of the ginsenoside glycosidase is preferably used. The incubation may be performed at a pH of 6.0 to 8.0, more preferably 6.5 to 7.5, most preferably about 7.0. The incubation temperature is 28 to 40° C., preferably 30 to 37° C. The incubation time is 12 to 72 hours, more preferably 24 hours to 36 hours.

After the reaction as described above, the purity of 20(S)—Rh2 may be increased by a conventional known additional purification process. According to one embodiment of the present invention, the purity of 20(S)—Rh2 is increased using recycling preparative HPLC.

The method of producing ginsenoside 20(S)—Rh2 comprising treating 20(S)—Rg3 with a ginsenoside glycosidase isolated from *Flavobacterium johnsoniae*, a transformant introduced with a vector comprising a nucleic acid encoding the ginsenoside glycosidase, or a culture of the transformant, according to the present invention, shows excellent 20(S)—Rh2 productivity, preferably under, but not limited to, conditions described below.

The method of producing 20(S)—Rh2 is performed under the same conditions as those described above with respect to the step (b) of the method of producing 20(S)—Rh2.

The present invention provides a composition for converting crude saponin to 20(S)—Rg3, the composition comprising either a ginsenoside glycosidase comprising an amino acid sequence represented by SEQ ID NO: 3, or a transformant introduced with a vector comprising a nucleic acid encoding the ginsenoside glycosidase protein, or a culture of the transformant.

The present invention provides a composition for converting crude saponin to 20(S)—Rh2, the composition comprising: a ginsenoside glycosidase comprising an amino acid sequence represented by SEQ ID NO: 3, a transformant introduced with a vector comprising a nucleic acid encoding the ginsenoside glycosidase protein, or a culture of the transformant; and a ginsenoside glycosidase comprising an amino acid sequence represented by SEQ ID NO: 4, a transformant introduced with a vector comprising a nucleic acid encoding the ginsenoside glycosidase protein, or a culture of the transformant.

Advantageous Effects

The method of producing of 20(S)—Rg3 or 20(S)—Rh2 according to the present invention can safely and efficiently produce 20(S)—Rg3 and 20(S)—Rh2, which are a minor form of rare ginsenosides present in very small amounts in ginseng or processed ginseng products. In particular, the method according to the present invention has an advantage in that it can produce a large amount of 20(S)—Rg3 or 20(S)—Rh2 for industrial applications, since the process is very simple and the production efficiency is very high.

DESCRIPTION OF DRAWINGS

FIG. 3A shows the results of analysis of a PPD-type ginsenoside mixture (crude saponin) of *Panax ginseng* C. A. Meyer; FIG. 3B shows the results of analysis performed at 48 hours after treatment with ginsenoside glycosidase (BglHg); and FIG. 3C shows the results of analysis performed at 24 hours after treatment with ginsenoside glycosidase (BglFj).

MODE FOR INVENTION

Hereinafter, the present invention will be described in more detail with reference to examples. However, these examples are merely to illustrate the present invention, and the scope of the present invention is not construed as being limited by these examples.

EXAMPLE 1

Extraction of Crude Saponin

The leaf and root of *Panax ginseng* C. A. Meyer was repeatedly extracted twice or more with a 20-fold volume of an ethanol having an alcohol content of 70% (v/v) at room temperature for 1 to 2 hours, followed by drying, thereby obtaining an extract. The extract was dissolved again in water, adsorbed onto HP-20 resin, and then washed with water to remove sugar. The washed extract was first washed with an ethanol having an alcohol content of 40% (v/v) to remove protopanaxatriol (PPT)-type ginsenoside Re and Rg1, and then washed with an ethanol having an alcohol content of 80% (v/v), and the fraction comprising eluted protopanaxadiol (PPD)-type ginsenoside Rb1, Rb2, Rc and Rd was collected and dried, thereby preparing a crude saponin extract.

EXAMPLE 2

Preparation of Novel Ginsenoside Glycosidases

EXAMPLE 2-1

Construction of Recombinant Expression Vectors and Transformed Microorganisms Comprising Novel Ginsenoside Glycosidase In order to prepare novel ginsenoside glycosidases capable of converting major ginsenosides to minor ginsenosides, novel ginsenoside glycosidases were isolated from *Herbiconiux ginsengi* KACC 14262T and *Flavobacterium johnsoniae* KACC 11414$^T$ strains, respectively.

Specifically, *Herbiconiux ginsengi* KACC 14262$^T$ and *Flavobacterium johnsoniae* KACC 11414$^T$ strains were selected, and genomic DNAs were extracted therefrom. Using each of the genomic DNAs as a template, polymerase chain reaction (PCR) was performed using each set of forward and reverse primers. The sequences of the primers are shown in Table 1 below.

TABLE 1

| Primers | Sequences (5'→3') |
|---|---|
| BglHg forward primer | GGTTCCGCGTGGATCCACAACCACACCCTCACTCACA (SEQ ID NO: 5) |
| BglHg reverse primer | GATGCGGCCGCTCGAGTTAGCCCTCGACCTCTTGTGA (SEQ ID NO: 6) |
| BglFj forward primer | CGGGATCCAAAAACAAATTAGTCTTACTTTTTTA (SEQ ID NO: 7) |

TABLE 1-continued

| Primers | Sequences (5'→3') |
|---|---|
| BglFj reverse primer | CCCCTCGAGCTATTTAGTTAACTCAAAACTAACTTT (SEQ ID NO: 8) |

Each of the fragments amplified by the reaction was sequenced, and as a result, the nucleotide sequence of the ginsenoside glycosidase derived from *Herbiconiux ginsengi* KACC 14262$^T$ was identified to have SEQ ID NO: 1, and the nucleotide sequence of the ginsenoside glycosidase derived from the *Flavobacterium johnsoniae* KACC 11414$^T$ strain was identified to have SEQ ID NO: 2. Each of the fragments amplified by the reaction was inserted into the plasmid vector pGEX4T-1 (GE Healthcare, USA) (having glutathione S-transferase inserted therein) using an EzCloning Kit (Enzynomics), thereby constructing two recombinant expression vectors, GST-BglHg (derived from *Herbiconiux ginsengi*) and GST-BglFj (derived from *Flavobacterium johnsoniae*). Each of the recombinant expression vectors was transformed into an *E. coli* BL21(DE3) strain by a conventional transformation method, thereby producing transformants comprising the ginsenoside glycosidase derived from the *Herbiconiux ginsengi* KACC 14262$^T$ or *Flavobacterium johnsoniae* KACC 11414$^T$ strain.

EXAMPLE 2-2

Isolation of Ginsenoside Glycosidase

In order to produce a large amount of a ginsenoside glycosidase from each of the transformants constructed in Example 2-1, each of the transformed strains was inoculated into an Erlenmeyer flask containing 100 ml of ampicillin-containing LB medium, and was seed-cultured in a shaking incubator at 200 rpm at 37° C. until the absorbance at 600 nm reached 0.6. In order to confirm expression of soluble protein at various temperatures (18, 22, 25, 30 and 37° C.), IPTG (isopropyl-beta-D-thiogalactoside) was added thereto to a final concentration of 0.1 mM in order to induce expression of a large amount of the ginsenoside glycosidase from each of the strains.

When each of the strain entered into the stationary phase, a culture of the strain was centrifuged at 6,000×g at 4° C. for 10 minutes, and suspended in 100 mM sodium phosphate buffer (pH 7.0), after which the cell suspension was lysed with a sonicator. The cell lysate was centrifuged again at 13,000×g at 4° C. for 15 minutes, and then a water-soluble ginsenoside glycosidase was isolated from the supernatant which could be used for ginsenoside production.

The isolated and purified ginsenoside glycosidases were analyzed by SDS-PAGE. The ginsenoside glycosidase derived from the *Herbiconiux ginsengi* KACC 14262$^T$ strain was named BglHg, and the ginsenoside glycosidase derived from the *Flavobacterium johnsoniae* KACC 11414$^T$ strain was named BglFj.

The ginsenoside glycosidase Bg1Hg was 740 amino acids in length, and the amino acid sequence thereof was represented by SEQ ID NO: 3. In addition, the ginsenoside glycosidase BglFj was 766 amino acids in length, and the amino acid sequence thereof was represented by SEQ ID NO: 4.

EXAMPLE 3

Examination of the Ability of Ginsenoside Glycosidases BglHg and BglFj to Biotransform Ginsenosides The crude saponin prepared in Example 1 above was dissolved in 50 mM sodium phosphate buffer (0.1% (w/v)), and then 0.2 U of the ginsenoside glycosidase (BglHg) was added thereto, followed by incubation under the conditions of pH 7.0 and 37° C. for 24 hours.

Meanwhile, in order to obtain ginsenoside 20(S)—Rh2, a portion of sample was collected at 12-hour intervals during the entire period of the reaction performed using the ginsenoside glycosidase (BglHg), and the collected sample was treated with the ginsenoside glycosidase (BglFj) and incubated for 24 hours.

The reaction was terminated by adding the same volume of aqueous solution-saturated butanol to each of the incubated solutions. The n-butanol fraction was dried and evaporated, and the residue was dissolved in $CH_3OH$.

Figure 1:
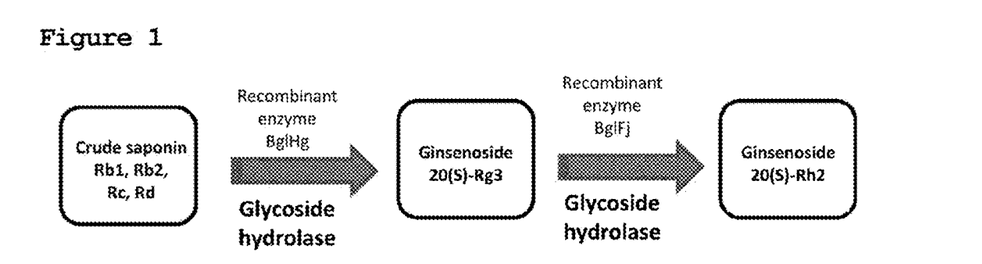
FIG. 1 schematically shows a method of producing ginsenosides according to the present invention.
Figure 2:
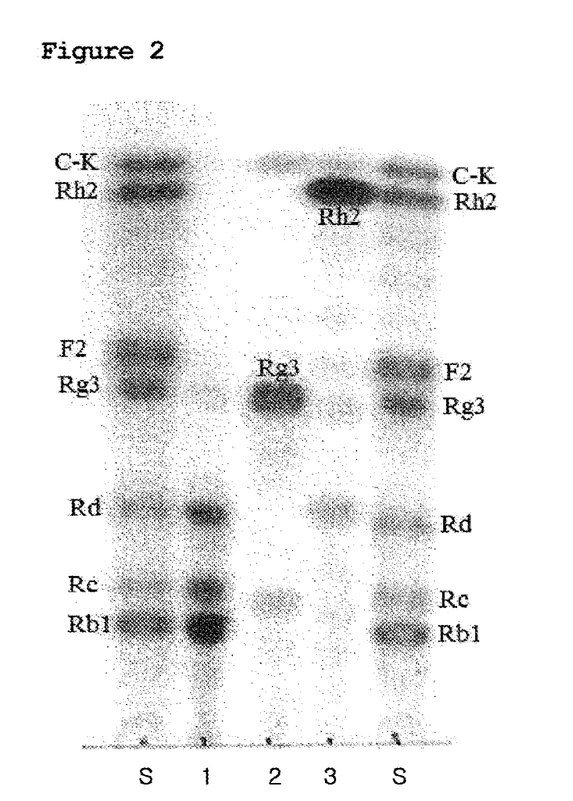
FIG. 2 shows the results of TLC analysis performed to confirm that a crude saponin comprising ginsenoside Rb1, Rc, Rd and the like was converted to ginsenoside 20(S)—Rg3 by ginsenoside BglHg, and then 20(S)—Rg3 was converted to 20(S)—Rh2 by treatment with BglFj: (S) standard; (1) crude saponin comprising PPD-type substrates; (2) 20(S)—Rg3 converted by ginsenoside BglHg; and (3) 20(S)—Rh2 converted by BglFj.

The solution was analyzed by TLC (thin layer chromatography), and the results are shown in FIG. 2.

As shown in FIG. 2, ginsenosides Rb1, Rc and Rd (1) were converted to ginsenoside 20(S)—Rg3 (2) by ginsenoside glycosidase BglHg, and then 20(S)—Rg3 was converted to 20(S)—Rh2 (3) by treatment with BglFj.

EXPERIMENTAL EXAMPLE

HPLC Analysis Conditions

HPLC was used to analyze the purities of ginsenosides 20(S)—Rg3 and Rh2. Gradient elution was performed using Prodigy ODS(2) $C_{18}$ column (5 μm, 150×4.6 mm I. D.; Phenomenex, USA) as a column, Eclips XDB $C_{18}$ (5 μm, 150×4.6 mm I. D.) as a guard column, and water(A) and acetonitrile(B) as a mobile phase. Each separated material was dissolved in methanol at a concentration of 1 mg/ml, and then 25 μl of the solution was injected, after which detection was performed at a flow rate of 1.0 ml/min and at 203 nm.

EXAMPLE 4

Production of Large Amount of Ginsenoside 20(S)—Rg3 Using Novel Ginsenoside Glycosidase (BglHg)

EXAMPLE 4-1

Obtaining of Enzyme Solution Comprising Ginsenoside Glycosidase (BglHg)

To obtain a large amount of an enzyme solution for producing 20(S)—Rg3 in large amounts of 100 g or more, a process of growing transformed E. coli cells in a 10-L unit fermentor was performed as follows. Prior to the main culture, transformed E. coli BL21(DE3) cells comprising GST-BglHg were inoculated and cultured in ampicillin-containing LB medium in 500-ml flask on the day before the main culture. On the next day, the cells were inoculated into a 6-L volume of LB (Luria-Bertani media) in a 10-L fermentor and cultured in a shaking incubator at 37° C. at 500 rpm until the absorbance at 600 nm reached 3. To induce expression of the water-soluble recombinant protein BglHg, the temperature of the fermentor was lowered to 25° C., and to facilitate the additional growth of the E. coli cells, 200 ml of a glucose solution (600 g/L) was added. 600 ml of 1 M sodium phosphate buffer was added to the thereto to keep the pH at around 7.0 under stable pH conditions. IPTG (isopropyl-beta-D-thiogalactoside) was added to thereto to a final concentration of 0.1 mM in order to induce expression of a large amount of ginsenoside glycosidase BglHg. The cells were cultured for 8 hours, and when the strain entered into the stationary phase, the culture medium of the strain was centrifuged at 6,000×g at 4° C. for 15 minutes, and 200 g of the E. coli were collected (about 30 g/L). The collected cells were suspended in 100 mM sodium phosphate buffer (pH 7.0), and the cell suspension was lysed with a sonicator. The cell lysate was centrifuged at 13,000×g at 4° C. for 15 minutes, thereby obtaining a large amount of the enzyme solution comprising BglHg expressed as a water-soluble protein.

EXAMPLE 4-2

Production of Large Amount of Ginsenoside 20(S)—Rg3

6 L of a PPD-type ginsenoside mixture (comprising Rb1, Rb2, Rc, Rd, etc.; crude saponin) having a maximum concentration of 5% was reacted with 2 L of the enzyme solution obtained in large amounts in Example 4-1 above at a temperature of 37° C. for 48 hours while stirring at 150 rpm.

Figure 3:
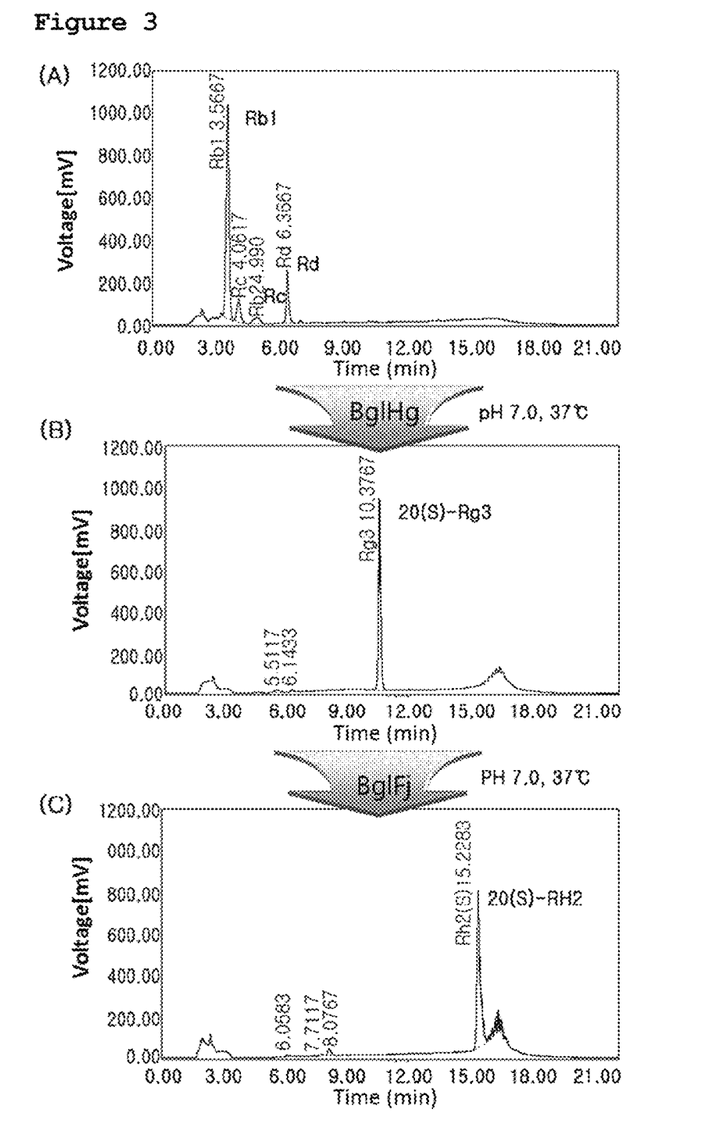
FIG. 3 shows the results of HPLC analysis performed to confirm that a crude saponin comprising ginsenoside Rb1, Rb2, Rc and Rd was converted to ginsenoside 20(S)—Rg3 by treatment with a ginsenoside glycosidase (Bg1Hg) from a *Herbiconiux ginsengi* strain and that 20(S)—Rg3 was converted to ginsenoside 20(S)—Rh2 by treatment with a ginsenoside glycosidase (BglFj) from a *Flavobacterium johnsoniae* strain. Specifically.

Meanwhile, before the reaction, HPLC analysis of the PPD-type ginsenoside mixture was performed as described in the Experimental Example, and the results are shown in FIG. 3A.

In order to stop the reaction and recover the converted 20(S)—Rg3, ethanol was added to thereto as to be 70%, thereby deactivating the recombinant enzyme to bring down and dissolving the ginsenoside 20(S)—Rg3. The alcohol concentration of the dissolved ginsenoside was again lowered, and the ginsenoside solution was adsorbed onto a HP20 porous resin, washed with water, desorbed with 80% ethanol, and then evaporated with a vacuum rotary evaporator, thereby obtaining highly pure ginsenoside 20(S)—Rg3. Finally, 250 g of the PPD mixture was reacted, thereby obtaining 142 g of high-concentration ginsenoside 20(S)—Rg3 which was then identified by TLC.

HPLC analysis of the obtained ginsenoside 20(S)—Rg3 was performed as described in the Experimental Example. The results are shown in FIG. 3B, and the results of the HPLC analysis showed that the purity was 75.4% based on the area ratio of the chromatogram, suggesting that 20(S)—Rg3 was produced at a significantly high rate.

EXAMPLE 4-3

Production of Ginsenoside 20(S)—Rg3 with 98% Purity

To increase the purity of the ginsenoside 20(S)—Rg3 obtained in Example 4-2 above, recycling preparative HPLC (Japan Analytical Instrument) was used. Specifically, 500 mg of 20(S)—Rg3 was dissolved in 75% ACN and fractionated using the solvent under the same conditions (75% ACN) at a rate of 7 ml/min on an ODS AP column (50σ×500 mm), thereby obtaining 240 mg of ginsenoside 20(S)—Rg3 having a purity corresponding to 99% based on the area ratio of the chromatogram.

EXAMPLE 5

Production of Large Amount of Ginsenoside 20(S)—Rh2 Using Novel Ginsenoside Glycosidase (BglFj)

EXAMPLE 5-1

Obtaining of Enzyme Solution Comprising Ginsenoside Glycosidase (BglFj)

A BglFj enzyme solution was obtained in the same manner as described in Example 4-1 (the method of producing a large amount of Bg1Hg enzyme solution) above.

EXAMPLE 5-2

Production of Large Amount of Ginsenoside 20(S)—Rh2

After completion of the reaction for conversion to 20(S)—Rg3 as described in Example 4-2 above, the reaction solution was heat-treated at 80° C. for about 1 hour, and the remaining BglHg enzyme was deactivated. Thereafter, 2 L of the BglFj enzyme solution was added to the reaction solution in which 20(S)—Rg3 dissolved, the mixture was reacted for 24 hours while stirring at 150 rpm at a temperature of 37° C. In order to stop the reaction and recover the converted 20(S)—Rh2, ethanol was added to thereto as to be 70%, thereby deactivating the recombinant enzyme to bring down and dissolving the ginsenoside 20(S)—Rh2. The alcohol concentration of the dissolved ginsenoside was again lowered, and the ginsenoside solution was adsorbed onto a HP20 porous resin, washed with water, desorbed with 80% ethanol, and then evaporated with a vacuum rotary evaporator, thereby obtaining highly pure ginsenoside 20(S)—Rh2. Finally, 250 g of the PPD mixture was reacted, thereby obtaining 110 g of ginsenoside 20(S)—Rh2 which was then identified by TLC.

HPLC analysis of the obtained ginsenoside 20(S)—Rh2 was performed as described in the Experimental Example. The results are shown in FIG. 3C, and the results of the HPLC analysis showed that the purity was 72.8% based on the area ratio of the chromatogram, suggesting that 20(S)—Rh2 was produced at a significantly high rate.

EXAMPLE 5-3

Production of Ginsenoside 20(S)—Rh2 with 98% Purity

To increase the purity of the ginsenoside 20(S)—Rh2 obtained in Example 5-2 above, recycling preparative HPLC (Japan Analytical Instrument) was used. Specifically, 500 mg of 20(S)—Rh2 was dissolved in 90% ACN and fractionated using the solvent under the same conditions at a rate of 7 ml/min on an ODS AP column (50σ×500 mm), thereby obtaining 235 mg of ginsenoside 20(S)—Rh2 having a purity corresponding to 99% based on the area ratio of the chromatogram.

The invention claimed is:

1. A method of producing ginsenoside 20(S)—Rg3 comprising: reacting ginseng crude saponin with
   a ginsenoside glycosidase having an amino acid sequence of at least 95% sequence similarity to the sequence of SEQ ID NO: 3.

2. The method of claim 1, wherein the amino acid sequence has at least 98% similarity to the sequence of SEQ ID NO: 3.

3. The method of claim 1, wherein the amino acid sequence is identical to the sequence of SEQ ID NO: 3.

4. The method of claim 1, wherein the ginsenoside glycosidase is expressed by a transformant introduced with a vector comprising a nucleic acid encoding the ginsenoside glycosidase having an amino acid sequence of at least 95% sequence similarity to the sequence of SEQ ID NO: 3.

5. The method of claim 4, wherein the ginseng crude saponin is reacted with a culture of the transformant containing the ginsenoside glycosidase.

6. The method of claim 1, wherein the reacting step is at a pH of 6.0 to 8.0 and a temperature of 28 to 40° C. for an incubation time of 12 to 72 hours.

7. A method of producing ginsenoside 20(S)—Rh2 comprising:
   (a) reacting ginseng crude saponin with
   a ginsenoside glycosidase having an amino acid sequence of at least 95% sequence similarity to the sequence of SEQ ID NO: 3 to prepare a reaction solution comprising ginsenoside 20(S)—Rg3; and
   (b) reacting the reaction solution prepared in the step (a) with
   a ginsenoside glycosidase having an amino acid sequence of at least 95% sequence similarity to the sequence of SEQ ID NO: 4 to produce ginsenoside 20(S)—Rh2.

8. The method of claim 7, wherein the ginsenoside glycosidase in the step (a) comprises an amino acid sequence that has at least 98% similarity to the sequence of SEQ ID NO: 3, and the ginsenoside glycosidase in the step (b) comprises an amino acid sequence that has at least 98% similarity to the sequence of SEQ ID NO: 4.

9. The method of claim 7, wherein the ginsenoside glycosidase in the step (a) comprises an amino acid sequence of SEQ ID NO: 3, and the ginsenoside glycosidase in the step (b) comprises an amino acid sequence of SEQ ID NO: 4.

10. The method of claim 7, wherein the ginsenoside glycosidase is expressed by a transformant introduced with a vector comprising a nucleic acid encoding the ginsenoside glycosidase having an amino acid sequence of at least 95% sequence similarity to the sequence of SEQ ID NO: 3, and the reaction solution prepared in the step (a) is reacted with ginsenoside glycosidase expressed by a transformant introduced with a vector comprising a nucleic acid encoding the ginsenoside glycosidase having an amino acid sequence of at least 95% sequence similarity to the sequence of SEQ ID NO: 4.

11. The method of claim 10, wherein the ginseng crude saponin is reacted with a culture of the transformant containing the ginsenoside glycosidase having an amino acid sequence of at least 95% sequence similarity to the sequence of SEQ ID NO: 3, and wherein the reaction solution prepared in the step (a) is reacted with a culture of the transformant containing the ginsenoside glycosidase having an amino acid sequence of at least 95% sequence similarity to the sequence of SEQ ID NO: 4.

12. The method of claim 7, wherein step (a) comprises reacting the crude ginseng crude saponin with the ginsenoside glycosidase having an amino acid sequence of at least 95% sequence similarity to the sequence of SEQ ID NO: 3 at a pH of 6.0 to 8.0 and a temperature of 28 to 40° C. for an incubation time of 12 to 72 hours, and wherein the treatment step (b) comprises reacting the crude ginseng crude saponin with the ginsenoside glycosidase having an amino acid sequence of at least 95% sequence similarity to the sequence of SEQ ID NO: 4 at a pH of 6.0 to 8.0 and a temperature of 28 to 40° C. for an incubation time of 12 to 72 hours.

13. The method of claim 12, further comprising, before the step (b), a step of performing deactivation of the ginsenoside glycosidase having an amino acid sequence of at least 95% sequence similarity to the sequence of SEQ ID NO: 3 by heating at 70° C. to 90° C. for at least 4 hours.

* * * * *

SEQUENCE LISTING

```
<160> NUMBER OF SEQ ID NOS: 8

<210> SEQ ID NO 1
<211> LENGTH: 2223
<212> TYPE: DNA
<213> ORGANISM: Artificial Sequence
<220> FEATURE:
<223> OTHER INFORMATION: DNA Sequence Ginsenoside glycosidase from
      Herbiconiux ginsengi

<400> SEQUENCE: 1
atgacaacca caccctcact cacactcgcg gagaaggcca gcctcggcag tggcgcagac      60
ttctggtcca ccaaagccct ccggggcatc ccttccgtct acctcaccga tggcccgcac     120
ggagttcgca aacaggggga cgctgtcgat catctcggag tctccatgag cgtccccgca     180
acctgcttcc ccctgccgc gggactgagt caatgttgga acagcgatct ggtcaggcag     240
gtcggcgcag cgctcgggcg agaagcacga gcgctcggcg tccatgtcct gctcggccca     300
ggtatcaaca tcaagcgaca cccactaggc ggacgcaact ttgagtactt ctcggaggac     360
ccaatcctta ctggagtgct tggtagcgct tgggttgacg ggatccagag cgagggtgtt     420
ggggcatccc tcaagcactt cgcagcgaat aatcaggaga gcgatcggca ccgaataagc     480
tccgacatcg accccgcac tctgcgggag gtttacctgc gcgcattcca gcgagtggtt     540
gaggtttcaa agccctggac cgtcatgtgc tcatacaacc gagtcaacaa cattcccgcg     600
tctgagagcg cattcctgct cacacgggta cttcgagatg actggaagtt cgacggcgtg     660
gtcgtcagcg attgggcgc ggtctctgat cgggtcgcgg ccgctcgcgc cggactcgac     720
ctagaaatgc ccgccgccga gggtagcgac gacaagctac tagacgccgc gatggacggt     780
tcgctcagtt cggcagtcct ggacagaatc gcggaacggg tcacagccct tgctcggaag     840
```

| | |
|---|---|
| gcgcgactca atgtgggtcg cgagaacgca gtcgacttcg acgcgaatca cgcgctcgcg | 900 |
| cgtgacgcgg cgacgcagag catcgtgttg ctgcgaaaca acaacggtct cctcccccta | 960 |
| actccgggcc agtcgattgc cgtaatcggt gaagctgcga gaacacctcg tttccagggc | 1020 |
| ggcggcagtt ccttcgtcaa tgccaagcgc gtcgatagcc cgctggacga gatccgacga | 1080 |
| atcggtggta ttgattcaat cgttttcgct gagggctacg ccagcgggga cagcatctcg | 1140 |
| agcggcgagt tgattgagga agcagtcgag gcagcgcgcg aggccgaggt agcagtgcta | 1200 |
| ttcctcgccg caccgctgga atccgaaggg atcgatcgca aagacctcga actccccgca | 1260 |
| gatcagattg cgctagcccg ggccgtactt gacgccaaca gcaacacaat cgttgttctc | 1320 |
| gcccggggtg gggcagtccg agttggaacg ttgggcccga tcccggcgat cctcgatggt | 1380 |
| gcgctactag gtcaaggaat cggcagagca atcgcagatg tcatctttgg gatcacgagt | 1440 |
| ccgtctggac ggctgtcgga aactgttccc ctgcggctcg aagacacgcc agcattcggc | 1500 |
| gcctttcctg cgagcatgg gcacgcccta tacggagagg gccttctggt tgggtaccgt | 1560 |
| tggtacgaca cacgaaaaat ggatgtcgag tacccattcg ccacggatt gtcctataca | 1620 |
| accttcgctt actccgaact ccaactcgcg gtcaccgatg aaggcataac cgccacggtg | 1680 |
| gtagtcacca acacaggtga ccaggcaggg cgtgaggtcc cccagttcta cgtatccgtc | 1740 |
| tcggattccg aagttacgcg tcccgcccaa gaactcaaag cgtttgacaa tgtgttcctc | 1800 |
| gaagtaggcg aatccaaagc cgtacaggtg cttcttcgcc gcggggatct cgcttattgg | 1860 |
| gacgtgcgag gcgataggtg gacgctagag agcggcgaat atatcgtctc cgtcggagcg | 1920 |
| tccagccgcg atatccgagc ccaatcaacg gtcctcgtcg aaggcgactt tgtattcgtc | 1980 |
| gagctgacta tgcactcgac aattggcgaa ctgctagcga acccggtgac caagagtgct | 2040 |
| atcgctaacg cactccaccac agctttcgga cctaccgaca acccggccgt gggtggaaat | 2100 |
| gtggtgcaga tgatctcgcc aagcccactc cactccgtta ttggattgct gggtgaggca | 2160 |
| cttgacgtag acaagttcca agtcctcctc gcaaccgcga actcacaaga ggtcgagggc | 2220 |
| taa | 2223 |

<210> SEQ ID NO 2
<211> LENGTH: 2301
<212> TYPE: DNA
<213> ORGANISM: Artificial Sequence
<220> FEATURE:
<223> OTHER INFORMATION: DNA Sequence Ginsenoside glycosidase from
      Flavobacterium johnsonia

<400> SEQUENCE: 2

| | |
|---|---|
| atgaaaaaca aattagtctt actttttta ggatgcgctg ttttgggtta cgctcaaaaa | 60 |
| aagccggcta aaatacagt gaaaattaaa ccaaagtctg aatttgtggc ggagttaatg | 120 |
| tcaaaaatga ctttagacga gaattgggt cagttaaacc tgccaacatc tggtgatatt | 180 |
| accacagggc aggcaaacag ctcaaatgtg caaaaaaca ttgctgaagg aaaagtgggt | 240 |
| ggtttgttta acattaaatc agttcaaaaa attaagaag tacagaaaat tgcggttgaa | 300 |
| aaaagccgtt taaaaattcc gctgcttttt ggtatggacg taattcacgg ttacgaaaca | 360 |
| acattcccaa ttccgttagg attatcttgt acctgggata tgggcttaat tgaaagaagt | 420 |
| gctcagattg ctgcaaaaga agcaagtgca gacggtatca actggacatt ttctccaatg | 480 |
| gttgatattt ctcgtgatcc aagatgggga agagtttctg aaggttcagg gaagatcca | 540 |
| tacttaggaa gccagattgc aaaagcaatg gtaaacggat atcagcagca tgatctttca | 600 |

```
aaaaataact caattttagc ttgtgttaag cacttcgcat tatacggtgc tccagaaggc    660
ggacgtgatt acaacacggt tgatatgagc cacatcagaa tgtttaatga ctattttcct    720
ccttacaaag cggcagttga tgctggtgta ggttcggtta tggcttcttt caacgaagtt    780
gacggaattc cagcaactgg aaacaaatgg ttaatgacag atgttttaag aaaacaatgg    840
gggttcaaag gatttgtagt aactgatttt acaggaattc ctgaaatgat cgaacacgga    900
atggggaatc ttcaagatgt ttctgcttta gcattaaatg ctggggttga atggatatg     960 gttggagaag gtttcttagg aactttgaaa aaatctttag acgaaggaag agtaaaaatc   1020
gaaacaatcg ataatgctgt aaaacttatt ttagaagcaa aatacgattt aggattattc   1080
caggacccat acaaatattg tgatgagaaa agagcaaaaa ctgaaatctt cacaactgac   1140
agcagaaaag aagcacgtga aattgcagca caatctttag ttttattaaa aaaccaaaac   1200
cagcttttac cacttaaaaa atctggaact attggtttaa tcggaccatt ggcagatgca   1260
aaagaaaaca tgccaggaac ttggagtgtg ctacaaaaaa tggaaaatgc cgtttcgtta   1320
ttgagaggta ttaaagaagt agccggagct ggaacaaaag ttttatatgc aaaaggaagt   1380
aatttagatt acgatgaaac ttttgaaacc aatgcgacaa tgtttggtaa aacattacac   1440
cgtgatgctc gttcaaaaga agatttatta gcagaagctt taaaagtagc ggagcagtca   1500
gatgtgattg tggcagcttt aggagaatct gcagaaatga gcggagaatc tagcagccgt   1560
acgaatttag aaattccaca agcgcaaaaa gatttattaa acgctttatt aaaaacagga   1620
aaaccagttg ttttagtttt atttgacgga cgtccgttag taattacaga cgaagagaaa   1680
acagttcctg caattttaaa tgcttggttc gcaggtacga aagctggtta tgctattgct   1740
gatgtattat tcggagacgt aaatccttca ggaaaattga cttcaacttt tccaagaagt   1800
gttgggcagc tgccaattta ctacgcgcac aaaaatacag gaagaccact ttctaataca   1860
gaaggtaaat tcgaaaaatt cagatcaaat tatattgacg aaagaaacga gccttatt c   1920 ccattcggat ttggttaag ctatacgact tttgattatt caaacctgaa aatttcttct    1980
gataaaatga atccatctgg aaaattgaaa gtaacagttg atttaactaa tacaggaaat   2040
tttgacggaa agaaacagt tcaattatat attagagatt tagttggttc agtaacaaga   2100
ccagttagag aattaaaagg tttccaaaaa atagcactta aaaaaggtga aaacaaacc   2160 gtaagttttg atattacggt tgaagattta aaattttata actctgattt gcaatttgca   2220
gcagagcctg gacagtttga tattttcgtt ggaggaaatt caaatgccga taagaaagtt   2280
agttttgagt taactaaata g                                             2301
```

<210> SEQ ID NO 3
<211> LENGTH: 740
<212> TYPE: PRT
<213> ORGANISM: Artificial Sequence
<220> FEATURE:
<223> OTHER INFORMATION: Amino Acid Sequence Ginsenoside glycosidase
      from Herbiconiux ginsengi

<400> SEQUENCE: 3

Met Thr Thr Thr Pro Ser Leu Thr Leu Ala Glu Lys Ala Ser Leu Gly
1               5                   10                  15

Ser Gly Ala Asp Phe Trp Ser Thr Lys Ala Leu Arg Gly Ile Pro Ser
            20                  25                  30

Val Tyr Leu Thr Asp Gly Pro His Gly Val Arg Lys Gln Gly Asp Ala
        35                  40                  45

Val Asp His Leu Gly Val Ser Met Ser Val Pro Ala Thr Cys Phe Pro

```
            50                  55                  60
Pro Ala Gly Leu Ser Gln Cys Trp Asn Ser Asp Leu Val Arg Gln
 65                  70                  75                  80

Val Gly Ala Ala Leu Gly Arg Glu Ala Arg Ala Leu Gly Val His Val
                 85                  90                  95

Leu Leu Gly Pro Gly Ile Asn Ile Lys Arg His Pro Leu Gly Gly Arg
                100                 105                 110

Asn Phe Glu Tyr Phe Ser Glu Asp Pro Ile Leu Thr Gly Val Leu Gly
                115                 120                 125

Ser Ala Trp Val Asp Gly Ile Gln Ser Glu Gly Val Gly Ala Ser Leu
130                 135                 140

Lys His Phe Ala Ala Asn Asn Gln Glu Ser Asp Arg His Arg Ile Ser
145                 150                 155                 160

Ser Asp Ile Asp Pro Arg Thr Leu Arg Glu Val Tyr Leu Arg Ala Phe
                165                 170                 175

Gln Arg Val Val Glu Val Ser Lys Pro Trp Thr Val Met Cys Ser Tyr
                180                 185                 190

Asn Arg Val Asn Asn Ile Pro Ala Ser Glu Ser Ala Phe Leu Leu Thr
                195                 200                 205

Arg Val Leu Arg Asp Asp Trp Lys Phe Asp Gly Val Val Ser Asp
210                 215                 220

Trp Gly Ala Val Ser Asp Arg Val Ala Ala Arg Ala Gly Leu Asp
225                 230                 235                 240

Leu Glu Met Pro Ala Ala Glu Gly Ser Asp Asp Lys Leu Leu Asp Ala
                245                 250                 255

Ala Met Asp Gly Ser Leu Ser Ser Ala Val Leu Asp Arg Ile Ala Glu
                260                 265                 270

Arg Val Thr Ala Leu Ala Arg Lys Ala Arg Leu Asn Val Gly Arg Glu
                275                 280                 285

Asn Ala Val Asp Phe Asp Ala Asn His Ala Leu Ala Arg Asp Ala Ala
                290                 295                 300

Thr Gln Ser Ile Val Leu Leu Arg Asn Asn Asn Gly Leu Leu Pro Leu
305                 310                 315                 320

Thr Pro Gly Gln Ser Ile Ala Val Ile Gly Glu Ala Ala Arg Thr Pro
                325                 330                 335

Arg Phe Gln Gly Gly Gly Ser Ser Phe Val Asn Ala Lys Arg Val Asp
                340                 345                 350

Ser Pro Leu Asp Glu Ile Arg Arg Ile Gly Gly Ile Asp Ser Ile Val
                355                 360                 365

Phe Ala Glu Gly Tyr Ala Ser Gly Asp Ser Ile Ser Ser Gly Glu Leu
                370                 375                 380

Ile Glu Glu Ala Val Glu Ala Arg Glu Ala Glu Val Ala Val Leu
385                 390                 395                 400

Phe Leu Ala Ala Pro Leu Glu Ser Glu Gly Ile Asp Arg Lys Asp Leu
                405                 410                 415

Glu Leu Pro Ala Asp Gln Ile Ala Leu Ala Arg Ala Val Leu Asp Ala
                420                 425                 430

Asn Ser Asn Thr Ile Val Val Leu Ala Arg Gly Ala Val Arg Val
                435                 440                 445

Gly Thr Leu Gly Pro Ile Pro Ala Ile Leu Asp Gly Ala Leu Leu Gly
                450                 455                 460

Gln Gly Ile Gly Arg Ala Ile Ala Asp Val Ile Phe Gly Ile Thr Ser
465                 470                 475                 480
```

```
Pro Ser Gly Arg Leu Ser Glu Thr Val Pro Leu Arg Leu Glu Asp Thr
            485                 490                 495
Pro Ala Phe Gly Ala Phe Pro Gly Glu His Gly His Ala Leu Tyr Gly
            500                 505                 510
Glu Gly Leu Leu Val Gly Tyr Arg Trp Tyr Asp Thr Arg Lys Met Asp
            515                 520                 525
Val Glu Tyr Pro Phe Gly His Gly Leu Ser Tyr Thr Thr Phe Ala Tyr
            530                 535                 540
Ser Glu Leu Gln Leu Ala Val Thr Asp Glu Gly Ile Thr Ala Thr Val
545                 550                 555                 560
Val Val Thr Asn Thr Gly Asp Gln Ala Gly Arg Glu Val Pro Gln Phe
                565                 570                 575
Tyr Val Ser Val Ser Asp Ser Glu Val Thr Arg Pro Ala Gln Glu Leu
                580                 585                 590
Lys Ala Phe Asp Asn Val Phe Leu Glu Val Gly Glu Ser Lys Ala Val
                595                 600                 605
Gln Val Leu Leu Arg Arg Gly Asp Leu Ala Tyr Trp Asp Val Arg Gly
            610                 615                 620
Asp Arg Trp Thr Leu Glu Ser Gly Glu Tyr Ile Val Ser Val Gly Ala
625                 630                 635                 640
Ser Ser Arg Asp Ile Arg Ala Gln Ser Thr Val Leu Val Glu Gly Asp
                645                 650                 655
Phe Val Phe Val Glu Leu Thr Met His Ser Thr Ile Gly Glu Leu Leu
                660                 665                 670
Ala Asn Pro Val Thr Lys Ser Ala Ile Ala Asn Ala Leu Thr Thr Ala
            675                 680                 685
Phe Gly Pro Thr Asp Asn Pro Ala Val Gly Gly Asn Val Val Gln Met
            690                 695                 700
Ile Ser Pro Ser Pro Leu His Ser Val Ile Gly Leu Leu Gly Glu Ala
705                 710                 715                 720
Leu Asp Val Asp Lys Phe Gln Val Leu Leu Ala Thr Ala Asn Ser Gln
                725                 730                 735
Glu Val Glu Gly
            740

<210> SEQ ID NO 4
<211> LENGTH: 766
<212> TYPE: PRT
<213> ORGANISM: Artificial Sequence
<220> FEATURE:
<223> OTHER INFORMATION: Amino Acid Sequence Ginsenoside glycosidase
      from Flavobacterium johnsoniae

<400> SEQUENCE: 4

Met Lys Asn Lys Leu Val Leu Leu Phe Leu Gly Cys Ala Val Leu Gly
1               5                   10                  15
Tyr Ala Gln Lys Lys Pro Ala Lys Asn Thr Val Lys Ile Lys Pro Lys
            20                  25                  30
Ser Glu Phe Val Ala Glu Leu Met Ser Lys Met Thr Leu Asp Glu Lys
        35                  40                  45
Leu Gly Gln Leu Asn Leu Pro Thr Ser Gly Asp Ile Thr Thr Gly Gln
    50                  55                  60
Ala Asn Ser Ser Asn Val Ala Lys Asn Ile Ala Glu Gly Lys Val Gly
65              70                  75                  80
Gly Leu Phe Asn Ile Lys Ser Val Gln Lys Ile Lys Glu Val Gln Lys
```

```
                    85                  90                  95
Ile Ala Val Glu Lys Ser Arg Leu Lys Ile Pro Leu Leu Phe Gly Met
                100                 105                 110

Asp Val Ile His Gly Tyr Glu Thr Thr Phe Pro Ile Pro Leu Gly Leu
            115                 120                 125

Ser Cys Thr Trp Asp Met Gly Leu Ile Glu Arg Ser Ala Gln Ile Ala
        130                 135                 140

Ala Lys Glu Ala Ser Ala Asp Gly Ile Asn Trp Thr Phe Ser Pro Met
145                 150                 155                 160

Val Asp Ile Ser Arg Asp Pro Arg Trp Gly Arg Val Ser Glu Gly Ser
                165                 170                 175

Gly Glu Asp Pro Tyr Leu Gly Ser Gln Ile Ala Lys Ala Met Val Asn
                180                 185                 190

Gly Tyr Gln Gln His Asp Leu Ser Lys Asn Asn Ser Ile Leu Ala Cys
                195                 200                 205

Val Lys His Phe Ala Leu Tyr Gly Ala Pro Glu Gly Gly Arg Asp Tyr
            210                 215                 220

Asn Thr Val Asp Met Ser His Ile Arg Met Phe Asn Asp Tyr Phe Pro
225                 230                 235                 240

Pro Tyr Lys Ala Ala Val Asp Ala Gly Val Gly Ser Val Met Ala Ser
                245                 250                 255

Phe Asn Glu Val Asp Gly Ile Pro Ala Thr Gly Asn Lys Trp Leu Met
                260                 265                 270

Thr Asp Val Leu Arg Lys Gln Trp Gly Phe Lys Gly Phe Val Val Thr
                275                 280                 285

Asp Phe Thr Gly Ile Pro Glu Met Ile Glu His Gly Met Gly Asn Leu
            290                 295                 300

Gln Asp Val Ser Ala Leu Ala Leu Asn Ala Gly Val Glu Met Asp Met
305                 310                 315                 320

Val Gly Glu Gly Phe Leu Gly Thr Leu Lys Lys Ser Leu Asp Glu Gly
                325                 330                 335

Arg Val Lys Ile Glu Thr Ile Asp Asn Ala Val Lys Leu Ile Leu Glu
                340                 345                 350

Ala Lys Tyr Asp Leu Gly Leu Phe Gln Asp Pro Tyr Lys Tyr Cys Asp
            355                 360                 365

Glu Lys Arg Ala Lys Thr Glu Ile Phe Thr Thr Asp Ser Arg Lys Glu
            370                 375                 380

Ala Arg Glu Ile Ala Ala Gln Ser Leu Val Leu Leu Lys Asn Gln Asn
385                 390                 395                 400

Gln Leu Leu Pro Leu Lys Lys Ser Gly Thr Ile Gly Leu Ile Gly Pro
                405                 410                 415

Leu Ala Asp Ala Lys Glu Asn Met Pro Gly Thr Trp Ser Val Ala Thr
            420                 425                 430

Lys Met Glu Asn Ala Val Ser Leu Leu Arg Gly Ile Lys Glu Val Ala
            435                 440                 445

Gly Ala Gly Thr Lys Val Leu Tyr Ala Lys Gly Ser Asn Leu Asp Tyr
            450                 455                 460

Asp Glu Thr Phe Glu Thr Asn Ala Thr Met Phe Gly Lys Thr Leu His
465                 470                 475                 480

Arg Asp Ala Arg Ser Lys Glu Asp Leu Leu Ala Glu Ala Leu Lys Val
                485                 490                 495

Ala Glu Gln Ser Asp Val Ile Val Ala Ala Leu Gly Glu Ser Ala Glu
                500                 505                 510
```

-continued

```
Met Ser Gly Glu Ser Ser Arg Thr Asn Leu Glu Ile Pro Gln Ala
        515                 520                 525

Gln Lys Asp Leu Leu Asn Ala Leu Leu Lys Thr Gly Lys Pro Val Val
530                 535                 540

Leu Val Leu Phe Asp Gly Arg Pro Leu Val Ile Thr Asp Glu Lys
545                 550                 555                 560

Thr Val Pro Ala Ile Leu Asn Ala Trp Phe Ala Gly Thr Glu Ala Gly
                565                 570                 575

Tyr Ala Ile Ala Asp Val Leu Phe Gly Asp Val Asn Pro Ser Gly Lys
                580                 585                 590

Leu Thr Ser Thr Phe Pro Arg Ser Val Gly Gln Leu Pro Ile Tyr Tyr
        595                 600                 605

Ala His Lys Asn Thr Gly Arg Pro Leu Ser Asn Thr Glu Gly Lys Phe
        610                 615                 620

Glu Lys Phe Arg Ser Asn Tyr Ile Asp Glu Arg Asn Glu Pro Leu Phe
625                 630                 635                 640

Pro Phe Gly Phe Gly Leu Ser Tyr Thr Thr Phe Asp Tyr Ser Asn Leu
                645                 650                 655

Lys Ile Ser Ser Asp Lys Met Asn Pro Ser Gly Lys Leu Lys Val Thr
                660                 665                 670

Val Asp Leu Thr Asn Thr Gly Asn Phe Asp Gly Lys Glu Thr Val Gln
        675                 680                 685

Leu Tyr Ile Arg Asp Leu Val Gly Ser Val Thr Arg Pro Val Arg Glu
        690                 695                 700

Leu Lys Gly Phe Gln Lys Ile Ala Leu Lys Lys Gly Glu Lys Gln Thr
705                 710                 715                 720

Val Ser Phe Asp Ile Thr Val Glu Asp Leu Lys Phe Tyr Asn Ser Asp
                725                 730                 735

Leu Gln Phe Ala Ala Glu Pro Gly Gln Phe Asp Ile Phe Val Gly Gly
                740                 745                 750

Asn Ser Asn Ala Asp Lys Lys Val Ser Phe Glu Leu Thr Lys
        755                 760                 765
```

<210> SEQ ID NO 5
<211> LENGTH: 37
<212> TYPE: DNA
<213> ORGANISM: Artificial Sequence
<220> FEATURE:
<223> OTHER INFORMATION: Forward primer of BglHg

<400> SEQUENCE: 5
ggttccgcgt ggatccacaa ccacaccctc actcaca      37

<210> SEQ ID NO 6
<211> LENGTH: 37
<212> TYPE: DNA
<213> ORGANISM: Artificial Sequence
<220> FEATURE:
<223> OTHER INFORMATION: Reverse primer of BglHg

<400> SEQUENCE: 6
gatgcggccg ctcgagttag ccctcgacct cttgtga      37

<210> SEQ ID NO 7
<211> LENGTH: 35
<212> TYPE: DNA
<213> ORGANISM: Artificial Sequence
<220> FEATURE:

```
<223> OTHER INFORMATION: Forward primer of BglFj

<400> SEQUENCE: 7
cgggatccaa aaacaaatta gtcttacttt tttta                            35

<210> SEQ ID NO 8
<211> LENGTH: 36
<212> TYPE: DNA
<213> ORGANISM: Artificial Sequence
<220> FEATURE:
<223> OTHER INFORMATION: Reverse primer of BglFj

<400> SEQUENCE: 8 ccccctcgagc tatttagtta actcaaaact aacttt                          36
```